United States Patent
Wang et al.

(10) Patent No.: US 10,745,434 B2
(45) Date of Patent: Aug. 18, 2020

(54) URIDINE PHOSPHORAMIDE PRODRUG, PREPARATION METHOD THEREFOR, AND MEDICINAL USES THEREOF

(71) Applicant: JIANGSU TASLY DIYI PHARMACEUTICAL CO., LTD., Jiangsu (CN)

(72) Inventors: Guocheng Wang, Jiangsu (CN); Huimin Wu, Jiangsu (CN)

(73) Assignee: JIANGSU TASLY DIYI PHARMACEUTICAL CO., LTD., Jiangsu (CN)

( * ) Notice: Subject to any disclaimer, the term of this patent is extended or adjusted under 35 U.S.C. 154(b) by 0 days.

(21) Appl. No.: 16/072,647

(22) PCT Filed: Mar. 22, 2017

(86) PCT No.: PCT/CN2017/077693
§ 371 (c)(1),
(2) Date: Jul. 25, 2018

(87) PCT Pub. No.: WO2017/162169
PCT Pub. Date: Sep. 28, 2017

(65) Prior Publication Data
US 2018/0371004 A1    Dec. 27, 2018

(30) Foreign Application Priority Data
Mar. 25, 2016 (CN) .......................... 2016 1 0180475

(51) Int. Cl.
| | | |
|---|---|---|
| *A01N 43/04* | (2006.01) | |
| *A61K 31/70* | (2006.01) | |
| *C07H 19/10* | (2006.01) | |
| *C07H 1/00* | (2006.01) | |
| *A61K 31/7072* | (2006.01) | |
| *A61P 31/14* | (2006.01) | |

(52) U.S. Cl.
CPC ......... *C07H 19/10* (2013.01); *A61K 31/7072* (2013.01); *A61P 31/14* (2018.01); *C07H 1/00* (2013.01)

(58) Field of Classification Search
None
See application file for complete search history.

(56) References Cited

U.S. PATENT DOCUMENTS

| | | | |
|---|---|---|---|
| 7,964,580 B2 * | 6/2011 | Sofia .................. | A61K 31/7072 514/51 |
| 9,156,874 B2 | 10/2015 | Huang et al. | |
| 2013/0210757 A1 * | 8/2013 | Huang ............................ | 514/47 |

FOREIGN PATENT DOCUMENTS

| | | |
|---|---|---|
| CN | 101918424 A | 12/2010 |
| CN | 102459299 A | 5/2012 |
| CN | 103665043 A | 3/2014 |
| CN | 103980332 A | 8/2014 |
| RU | 2466729 C2 | 11/2012 |
| WO | WO 2008/121634 A2 | 10/2008 |
| WO | WO 2013/187978 A1 | 12/2013 |
| WO | WO 2014/032481 A1 | 3/2014 |

OTHER PUBLICATIONS

Dudareva et al. The Plant Journal (1998), vol. 14, pp. 297-304.*
International Patent Application No. PCT/CN2017/077693; Int'l Search Report; dated Jun. 30, 2017; 3 pages.
Pradere et al.; "Synthesis of Nucleoside Phosphate and Phosphonate Prodrugs"; Chemical Reviews; vol. 114; 2014; p. 9154-9218.
Peng et al.; "Discovery of an Orally Active and Liver-Targeted Prodrug of 5-Fluoro-2'-Deoxyuridine for the Treatment of Hepatocellular Carcinoma"; Journal of Medicinal Chemistry; vol. 59; 2016; p. 3661-3670.
European Patent Application No. 17769446.0; Extended Search Report; dated Oct. 15, 2019; 5 pages.

* cited by examiner

Primary Examiner — Patrick T Lewis
(74) Attorney, Agent, or Firm — Baker & Hostetler LLP (57) ABSTRACT

The present invention relates to a uridine phosphoramide prodrug, the preparation method therefor, and the medicinal uses thereof. The prodrug of the present invention is a chemical compound as shown in formula I, an optical isomer thereof or a pharmaceutically acceptable salt thereof. The prodrug of the present invention further comprises a solvate of the chemical compound shown in formula I, of an optical isomer thereof or of a pharmaceutically acceptable salt thereof. The prodrug of the present invention can treat viral infectious diseases, particularly hepatitis C viral infectious diseases.

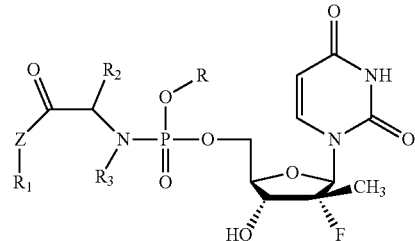

Formula I

5 Claims, 5 Drawing Sheets

01 R₄ = H, R₅ = H
02 R₄ = Me, R₅ = H
03 R₄ = OMe, R₅ = H
04 R₄ = H, R₅ = Me
05 R₄ = H, R₅ = OMe

URIDINE PHOSPHORAMIDE PRODRUG, PREPARATION METHOD THEREFOR, AND MEDICINAL USES THEREOF

CROSS-REFERENCE TO RELATED APPLICATIONS

This application is the National Stage of International Application No. PCT/CN2017/077693 filed Mar. 22, 2017, which claims the benefit of Chinese application number CN201610180475.2, filed Mar. 25, 2016, the disclosures of which are incorporated herein by reference in their entireties.

TECHNICAL FIELD

The present invention relates to a novel uridine phosphoramide prodrug or an isomer, a pharmaceutically acceptable salt, a hydrate and a solvate thereof, and a preparation method therefor, and medicinal uses thereof.

BACKGROUND ART

Hepatitis C is a global epidemic disease. At present, there are more than 200 million patients with hepatitis C, including tens of millions patients in China. NS5B inhibitors, which are polymerase inhibitors, can interfere with virus replication by binding with NS5B RNA-dependent RNA polymerase. Such drugs are classified into nucleoside inhibitors and non-nucleoside inhibitors. The nucleoside inhibitor, also known as active site inhibitors, can be intercalated into the RNA strand in the disguise of natural substrates of the polymerase to interrupt the replication of the RNA. Therefore, such drugs can combat HCV infections of all genotypes, and the antibiotic resistance of the virus thereto is very low. Among them, 2-fluoro-2-methyldeoxyuridine triphosphoric acid is an intracellular potent NS5B inhibitor, but cannot be transported to the lesion in vivo. Thus, a prodrug of its inactive form 2-fluoro-2-methyldeoxyuridine monophosphate can be used, which may be metabolized into the 2-fluoro-2-methyldeoxyuridine monophosphate and then activated into 2-fluoro-2-methyldeoxyuridine triphosphoric acid in vivo, thereby inhibiting the NS5B and playing an anti-HCV effect.

Currently, a strategy of adding a masking group to a phosphate group to form a prodrug is adopted, wherein a chemical compound containing one masking group forming a phosphoramide structure with the phosphate group and the other group forming a phosphate ester with the phosphate group has been proven to have the liver targeting effect. Ester-forming groups include various aromatic rings and heteroaromatic rings used in tenofovir prodrugs, especially phenol esters (CN201310041647.4, WO02082841), but the synthesis and bioactivity of an ester-forming group as a prodrug of 2-fluoro-2-methyldeoxyuridine monophosphate of a relatively non-toxic benzyl, natural alcohol, saccharide, or vitamin.

The present invention aims to provide a novel uridine monophosphoramide prodrug compound, a preparation method thereof, and uses thereof in the preparation of a drug for the treatment of viral infectious diseases so as to simultaneously improve the liver targeting ability and the bioavailability of the drug, thus improving the therapeutic effect of the drug and reducing the dosage and the toxicity of the drug.

SUMMARY OF THE INVENTION

The inventors have invented uridine phosphoramide prodrug compounds. The compounds of the present invention can be efficiently metabolized and phosphorylated into an active product 2-fluoro-2-methyldeoxyuridine triphosphoric acid in the liver after intragastric administration to rats. Moreover, compared with the prior art, the compounds of the present invention are more stable in plasma and the active metabolite 2-fluoro-2-methyldeoxyuridine triphosphoric acid thereof is completely undetectable in plasma, thereby reducing the systemic toxic side effects caused by the presence of the active metabolite in non-target organs due to plasma metabolization.

The present invention aims to provide an antiviral uridine phosphoramide prodrug, which is a chemical compound as shown in formula I, an optical isomer thereof, or a pharmaceutically acceptable salt thereof.

Formula I

In the formula:

R is independently selected from substituted or unsubstituted benzyl groups, substituted or unsubstituted $C_5$-$C_{50}$ linear or cyclic natural product fragments, or is selected from semi-synthetic or full-synthetic saccharides, vitamins, alcohols, and analogue fragments thereof after being structurally transformed and modified;

$R_1$, $R_2$ and $R_3$ are each independently selected from H, substituted or unsubstituted $C_1$-$C_{10}$ linear hydrocarbyl, $C_3$-$C_{10}$ branched hydrocarbyl, $C_3$-$C_{10}$ cyclic hydrocarbyl, $C_6$-$C_{10}$ aryl or heteroaryl, wherein the substituents are one to three heteroatoms independently selected from O, S, N and Se, or substituted or unsubstituted 3 to 8-membered rings formed by $R_1$ and $R_2$, $R_1$ and $R_3$, and $R_2$ and $R_3$ together with the structural parts to which they are attached; and Z is independently selected from O, S, Se, —NH—, or —CH$_2$—.

The prodrug further includes a solvate of the chemical compound as shown in formula I or a pharmaceutically acceptable salt thereof, and an optical isomer thereof.

Preferably, in the prodrug of the present invention:

R is independently selected from substituted or unsubstituted benzyl groups, or selected from linear or cyclic natural products with the parent nucleus of $C_3$-$C_8$, or selected from semi-synthetic or full-synthetic saccharides, vitamins, alcohols, and analogue fragments thereof after being structurally transformed and modified;

$R_1$, $R_2$ and $R_3$ are each independently selected from H, substituted or unsubstituted $C_1$-$C_{10}$ linear hydrocarbyl, $C_3$-$C_{10}$ branched hydrocarbyl, $C_3$-$C_{10}$ cyclic hydrocarbyl, $C_6$-$C_{10}$ aryl or heteroaryl, wherein the substituents are one to three heteroatoms independently selected from O, S, N and Se, or substituted or unsubstituted 3 to 8-membered rings formed by $R_1$ and $R_2$, $R_1$ and $R_3$, and $R_2$ and $R_3$ together with the structural parts to which they are attached; and Z is independently selected from O, S, Se, —NH—, or —CH$_2$—.

Preferably, in the prodrug of the present invention:

R is independently selected from substituted or unsubstituted benzyl groups, or selected from natural products with the parent nucleus of $C_3$-$C_8$, the natural products being selected from various monosaccharides or analogue fragments thereof, or from various polysaccharides or analogue fragments thereof, or from lipid-soluble vitamins, or from natural alcohols or analogues thereof;

$R_1$, $R_2$ and $R_3$ are each independently selected from H, substituted or unsubstituted $C_1$-$C_{10}$ linear hydrocarbyl, $C_3$-$C_{10}$ branched hydrocarbyl, $C_3$-$C_{10}$ cyclic hydrocarbyl, $C_6$-$C_{10}$ aryl or heteroaryl, wherein the substituents are one to three heteroatoms independently selected from O, S, N and Se, or substituted or unsubstituted 3 to 8-membered rings formed by $R_1$ and $R_2$, $R_1$ and $R_3$, and $R_2$ and $R_3$ together with the structural parts to which they are attached; and Z is independently selected from O, S, Se, —NH—, or —$CH_2$—.

Preferably, in the prodrug of the present invention:

R is independently selected from substituted or unsubstituted benzyl groups, or selected from natural products with the parent nucleus of $C_3$-$C_8$, the natural products being selected from various monosaccharides or analogue fragments thereof, or from various polysaccharides or analogue fragments thereof, or from lipid-soluble vitamins, or from natural alcohols or analogues thereof;

$R_1$, $R_2$ and $R_3$ are each independently selected from H, substituted or unsubstituted $C_1$-$C_{10}$ linear hydrocarbyl, $C_3$-$C_{10}$ branched hydrocarbyl, $C_3$-$C_{10}$ cyclic hydrocarbyl, $C_6$-$C_{10}$ aryl or heteroaryl, wherein the substituents are one to three heteroatoms independently selected from O, S, N and Se, or substituted or unsubstituted 3 to 8-membered rings formed by $R_1$ and $R_2$, $R_1$ and $R_3$, and $R_2$ and $R_3$ together with the structural parts to which they are attached; and Z is O or S.

Preferably, in the prodrug of the present invention:

R is independently selected from benzyl groups containing unsubstituted benzene rings, or benzyl groups containing unsubstituted methylene, or benzyl groups containing benzene rings with substituents independently selected from ortho- or para-substituted $C_1$-$C_{10}$ linear hydrocarbyl, $OC_1$-$C_{10}$ alkoxyhydrocarbyl, $C_3$-$C_{10}$ branched hydrocarbyl, $C_3$-$C_{10}$ cyclic hydrocarbyl, $C_6$-$C_{10}$ aryl or heteroaryl, or benzyl groups containing methylene with substituents independently selected from $C_1$-$C_{10}$ linear hydrocarbyl, $OC_1$-$C_{10}$ alkoxyhydrocarbyl, $C_3$-$C_{10}$ branched hydrocarbyl, $C_3$-$C_{10}$ cyclic hydrocarbyl, $C_6$-$C_{10}$ aryl or heteroaryl, or selected from various monosaccharides with the parent nucleus of $C_3$-$C_8$ or analogue fragments thereof, or from various polysaccharides or analogue fragments thereof, or from lipid-soluble vitamins, or from natural alcohols or analogues thereof;

$R_1$, $R_2$ and $R_3$ are each independently selected from H, substituted or unsubstituted $C_1$-$C_{10}$ linear hydrocarbyl, $C_3$-$C_{10}$ branched hydrocarbyl, $C_3$-$C_{10}$ cyclic hydrocarbyl, $C_6$-$C_{10}$ aryl or heteroaryl, wherein the substituents are one to three heteroatoms independently selected from O, S, N and Se, or substituted or unsubstituted 3 to 8-membered rings formed by $R_1$ and $R_2$, $R_1$ and $R_3$, and $R_2$ and $R_3$ together with the structural parts to which they are attached; and Z is O or S.

Preferably, in the prodrug of the present invention:

R is independently selected from benzyl groups containing unsubstituted benzene rings, or benzyl groups containing unsubstituted methylene, or benzyl groups containing benzene rings with substituents independently selected from methyl or/and methoxy, or benzyl groups containing methylene with substituents independently selected from $C_1$-$C_{10}$ linear hydrocarbyl, $OC_1$-$C_{10}$ alkoxyhydrocarbyl, $C_3$-$C_{10}$ branched hydrocarbyl, $C_3$-$C_{10}$ cyclic hydrocarbyl, $C_6$-$C_{10}$ aryl or heteroaryl, wherein when there is only one substitute on the benzene ring of a benzyl group and in the ortho-position, the substituent is non-methyl;

$R_1$ is isopropyl;

$R_2$ is methyl, and the carbon atom configuration attached thereto is R or S;

$R_3$ is H; and

Z is O.

Preferably, in the prodrug of the present invention:

R is independently selected from benzyl groups containing unsubstituted benzene rings, or selected from benzyl groups containing benzene rings with substituents as methyl or/and methoxy, wherein when there is only one substitute on the benzene ring of a benzyl group and in the ortho-position, the substituent is non-methyl;

$R_1$ is isopropyl;

$R_2$ is methyl, and the carbon atom configuration attached thereto is R or S;

$R_3$ is H; and

Z is O.

More preferably, in the prodrug of the present invention:

R is independently selected from benzyl groups containing unsubstituted benzene rings, or selected from benzyl groups containing benzene rings with substituents as methyl or/and methoxy, wherein when there is only one substitute on the benzene ring of a benzyl group and in the ortho-position, the substituent is non-methyl;

$R_1$ is isopropyl;

$R_2$ is methyl, and the carbon atom configuration attached thereto is S-configuration;

$R_3$ is H; and

Z is O.

The prodrugs of the present invention are, particularly preferably, chemical compounds of the following structures, optical isomers thereof, pharmaceutically acceptable salts thereof, or solvents of the chemical compounds, the optical isomers thereof, or the pharmaceutically acceptable salts thereof:

01

According to the prodrug of the present invention, the pharmaceutically acceptable salt of the chemical compound of formula I includes a salt formed with an inorganic acid such as hydrohalic acid, sulfuric acid, a salt formed with an organic salt such as acetic acid, trifluoroacetic acid, citric acid, maleic acid, oxalic acid, succinic acid, benzoic acid, tartaric acid, fumaric acid, mandelic acid, ascorbic acid or malic acid, and a salt formed with an amino acid such as alanine, aspartic acid, lysine, or a salt formed with a sulfonic acid such as methanesulfonic acid, p-toluenesulfonic acid. The compounds also be prepared into alkali metal salts, alkaline earth metal salts, silver salts, barium salts, etc., such as potassium salts, sodium salts, ammonium salts, calcium salts, magnesium salts, according to requirements and the properties of the compounds.

The chemical compound of formula I of the present invention can also be present in the form of solvates (e.g. hydrates), and therefore, such solvates (e.g. hydrates) are also included in the chemical compounds of the present invention.

The present invention further involves a preparation method for the prodrug. A first equation of the method is as follows and shown in FIG. 1.

Figure 1:
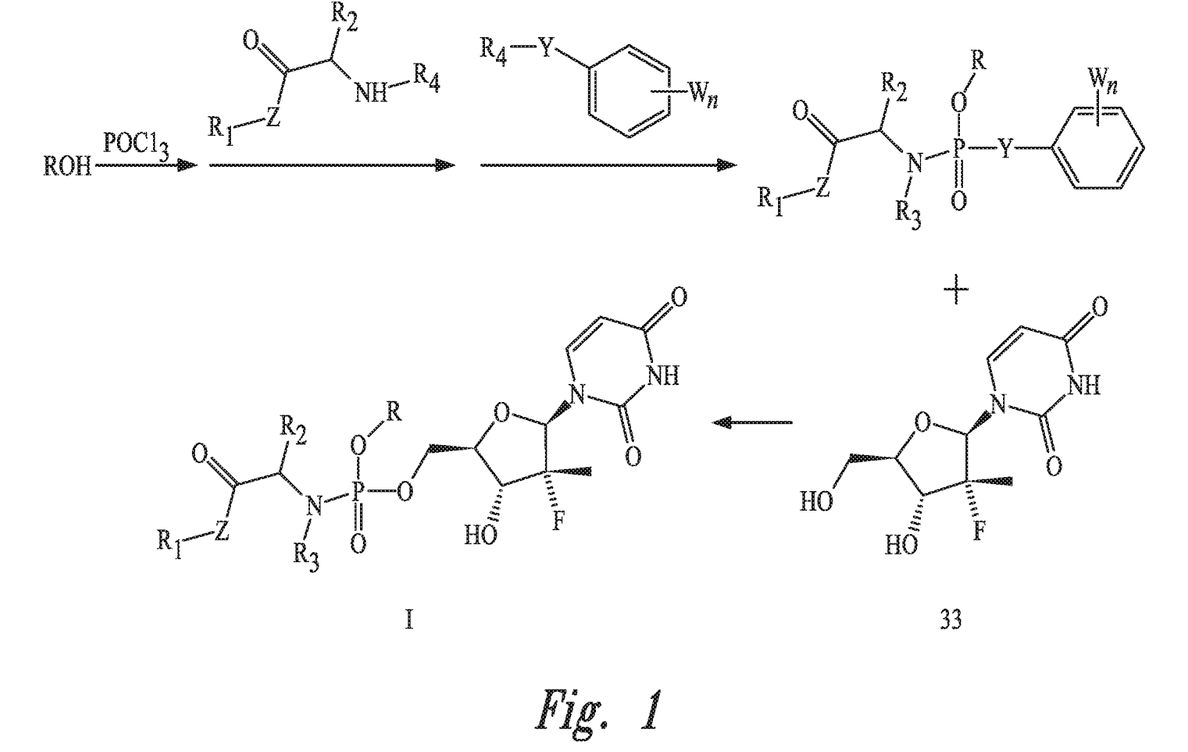
FIG. 1 shows a first equation of the method.

1.1) Phosphorus oxychloride reacts with a hydroxyl-containing alcohol or saccharide or a benzyl-containing compound in the presence of a base, and then reacts with an amino acid ester and an active aromatic reagent containing a benzene ring to obtain an active phosphate ester intermediate, wherein Y is O atom, S atom, or Se atom; $R_4$ is hydrogen atom or any silicon-containing or fluorine-containing active leaving group; W is any halogen atom or a nitro-group; and n is an arbitrary integer from 0 to 5.

1.2) The phosphate ester intermediate reacts with a uridine analogue 33 in the presence of a base to generate a uridine phosphoramide prodrug as shown in formula I.

In the step 1.1):
the base is an inorganic base or an organic base, preferably an organic base, and the organic base is further preferably an amine compound, such as but not limited to diisopropylethylamine, triethylamine, tert-butylamine, diethylamine and the like; and
the benzyl-containing compound refers to various substituted or unsubstituted benzyl halides or benzyl alcohols, more preferably various substituted or unsubstituted benzyl bromides or various substituted or unsubstituted benzyl alcohols.

Figure 2:
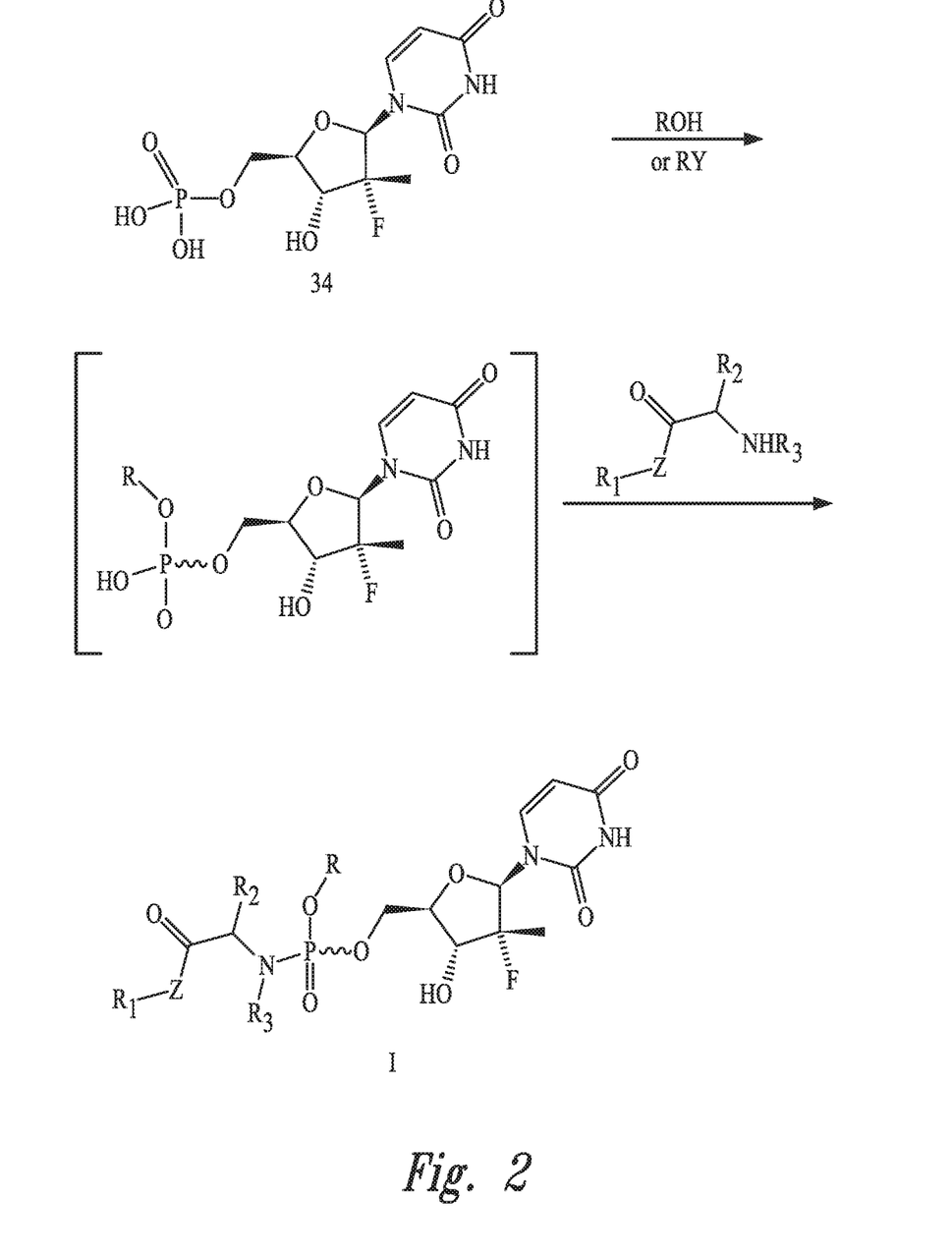
FIG. 2 shows the second equation of the method.

In the step 1.2):
the base is an inorganic base or an organic base, preferably an organic base, and the organic base is further preferably an amine compound, such as but not limited to diisopropylethylamine, triethylamine, tert-butylamine, diethylamine and the like; and A second equation of the method is as follows and shown in FIG. 2.

2.1) A uridine monophosphate compound 34 reacts with a hydroxyl-containing alcohol or saccharide or a compound with a benzyl group in the presence of a base to obtain a uridine monophosphate intermediate.

2.2) The uridine monophosphate intermediate reacts with a cyclic compound containing —NH— group in an NH— group-terminated compound molecule in the presence of a condensing agent to generate a uridine phosphoramide prodrug as shown in formula I.

In the step 2.1):
the base is an inorganic base or an organic base, preferably an organic base, and the organic base is further preferably an amine compound, such as but not limited to diisopropylethylamine, triethylamine, tert-butylamine, diethylamine and the like; and
the benzyl-containing compound refers to various substituted or unsubstituted benzyl halides or benzyl alcohols, preferably various substituted or unsubstituted benzyl bromides or various substituted or unsubstituted benzyl alcohols.

In the step 2.2):
the base is an inorganic base or an organic base, preferably an organic base, and the organic base is further preferably an amine compound, such as but not limited to diisopropylethylamine, triethylamine, tert-butylamine, diethylamine and the like; and The present invention further involves a chiral separation method for compounds, wherein eluates retained for various time are collected after separation by an HPLC reversed phase preparative column or separation by a chiral column.

The present invention further involves a pharmaceutical composition containing the prodrug of the present invention and a pharmaceutically acceptable carrier. The prodrug can treat viral infectious diseases, such as hepatitis C or diseases induced by hepatitis C virus.

The pharmaceutical composition of the present invention is preferably in the form of the pharmaceutical composition disclosed by the invention is preferably in the form of a unit-dose pharmaceutical preparation, and can be prepared into any pharmaceutical formulation when being prepared into the pharmaceutical preparation, wherein such formulations are selected from tablets, sugar-coated tablets, film-coated tablets, enteric-coated tablets, capsules, hard capsules, soft capsules, oral liquid, buccal tablets, granules, suspensions, solutions, injections, suppositories, ointments, plasters, creams, sprays, patches. The form of the oral preparation is preferred, and the form of tablets or capsules is most preferred.

Further, the pharmaceutical composition of the present invention also contains a pharmaceutically acceptable carrier.

The pharmaceutical preparation can be prepared by using a conventional pharmaceutical technique, for example, mixing the novel uridine phosphoramide prodrug compound of the present invention, a hydrate thereof, a solvate thereof, a pharmaceutically acceptable salt thereof or a resolved single isomer thereof with a pharmaceutically acceptable carrier. The pharmaceutically acceptable carrier includes, but is not limited to, mannitol, sorbitol, sorbic acid or a potassium salt, sodium pyrosulfite, sodium hydrogen sulfite, sodium thiosulfate, cysteine hydrochloride, mercaptoacetic acid, methionine, vitamin A, vitamin C, vitamin E, vitamin D, azone, disodium-EDTA, EDTA (ethylene diamine tetraacetic acid) calcium sodium, calcium sodium EDTA, carbonates, acetates and phosphates of a monovalent alkali metal or aqueous solutions thereof, hydrochloric acid, acetic acid, sulfuric acid, phosphoric acid, amino acids, sodium chloride, potassium chloride, sodium lactate, xylitol, maltose, glucose, fructose, fructose, dextran, glycine, starch, sucrose, lactose, mannitol, silicon derivatives, cellulose and derivatives thereof, alginate, gelatin, polyvinylpyrrolidone, glycerol, propylene glycol, ethanol, tween 60-80, span-80, beeswax, wool fat, liquid paraffin, hexadecanol, gallic acid ester, agar, triethanolamine, basic amino acids, urea, allantoin, calcium carbonate, calcium bicarbonate, polyethylene glycol, cyclodextrin, beta-cyclodextrin, phospholipid materials, kaolin, talcum powder, calcium stearate, magnesium stearate, etc.

When the pharmaceutical preparation of the present invention is prepared into a medicament, the medicament in unit dose may contain 0.1-1000 mg pharmaceutical active substance of the present invention and the balance of a pharmaceutically acceptable carrier. The pharmaceutically acceptable carrier may account for 0.1-99.9% of the total weight of the preparation by weight.

In use, the usage and dosage of the pharmaceutical preparation of the present invention are determined according to conditions of patients.

Terms used herein will be explained below.

The monosaccharides or analogues thereof include, but are not limited to, ribose, deoxyribose, arabinose, glucose, xylose, rhamnose, glucose, mannose and the like.

The polysaccharides or analogue fragments thereof are, such as but not limited to, sucrose, lactose, maltose, cellobiose and the like.

The fat-soluble vitamins refer to vitamins which are insoluble in water and soluble in fats and organic solvents, including vitamin A, vitamin D, vitamin E and vitamin K.

The natural alcohols or analogues thereof are, such as but not limited to, resveratrol, flavonol, menthol and the like.

The compounds provided in the present invention have the following advantages:

1. In structure, compared with the sofosbuvir structure, and the phenyl group in the sofosbuvir structure is replaced by less toxic benzyl, natural alcohols, natural saccharides or vitamins, so that the metabolic fragments are changed from phenol with relatively high neurotoxicity and cardiotoxicity into relatively non-toxic benzyl alcohol, natural alcohol, natural saccharide or vitamin compounds.

2. In effect, the compounds provided in the present invention can be efficiently metabolized and phosphorylated into an active product 2-fluoro-2-methyldeoxyuridine triphosphoric acid in the liver after intragastric administration to rats, and the active metabolite is completely undetectable in blood. Moreover, compared with the prior art, the compounds provided in the present invention can be more stable in human plasma, thereby reducing the systemic toxic side effects caused by the presence of the active metabolite in non-target organs due to plasma metabolization while maintaining the bioactivity of the compounds.

DETAILED DESCRIPTION OF THE INVENTION

The present invention will be explained in detail in conjunction with specific examples so that those skilled in the art can fully) understand the present disclosure. Synthesis routes and specific examples are merely meant to illustrate the technical solutions of the present invention and not intended to limit the present invention in any manner.

Figure 3A:
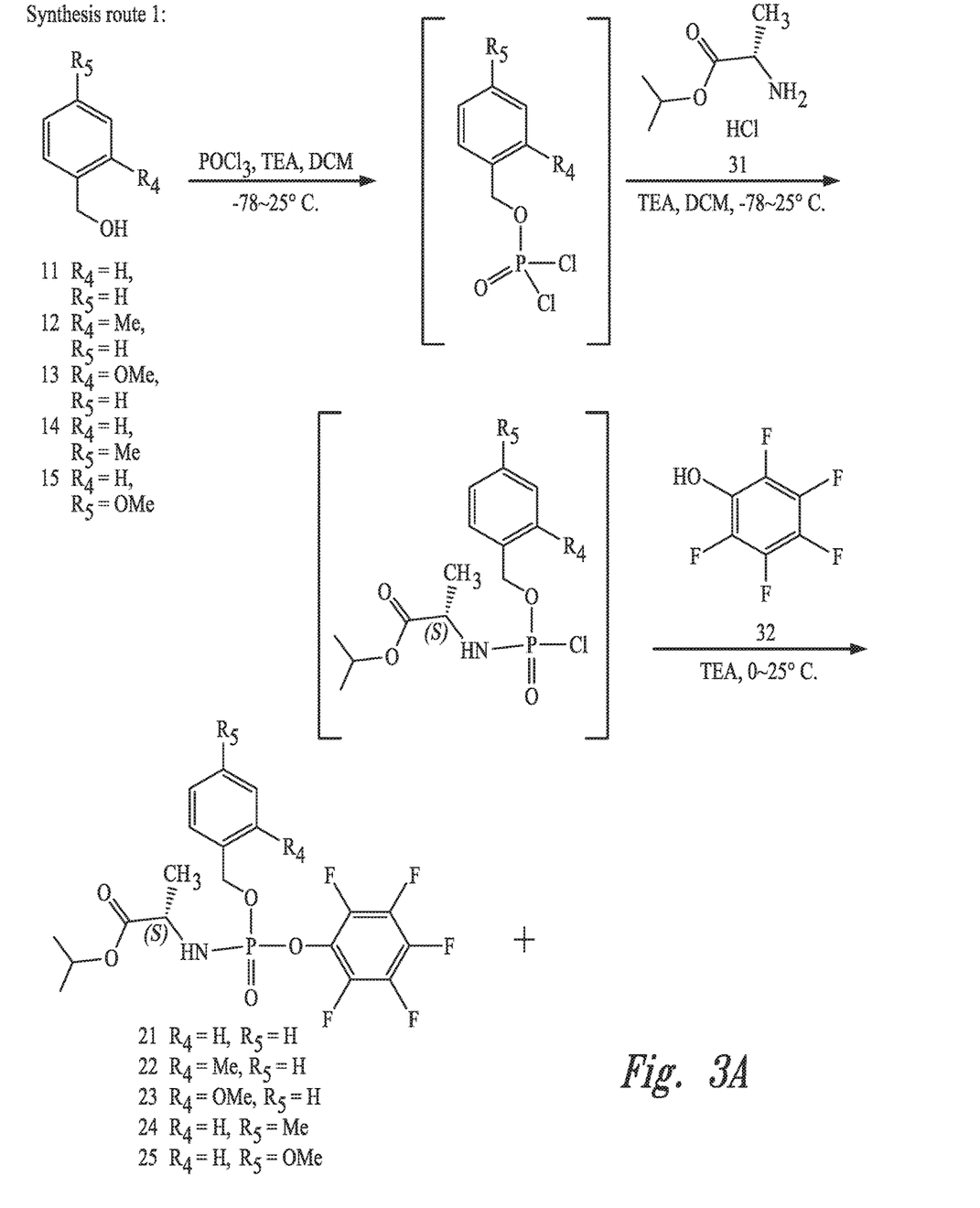
FIG. 3A shows synthesis route 1, and generation of an intermediate compound selected from the group consisting of compounds 21, 22, 23, 24, and 25, as disclosed in Examples 1 to 5.
Figure 3B:
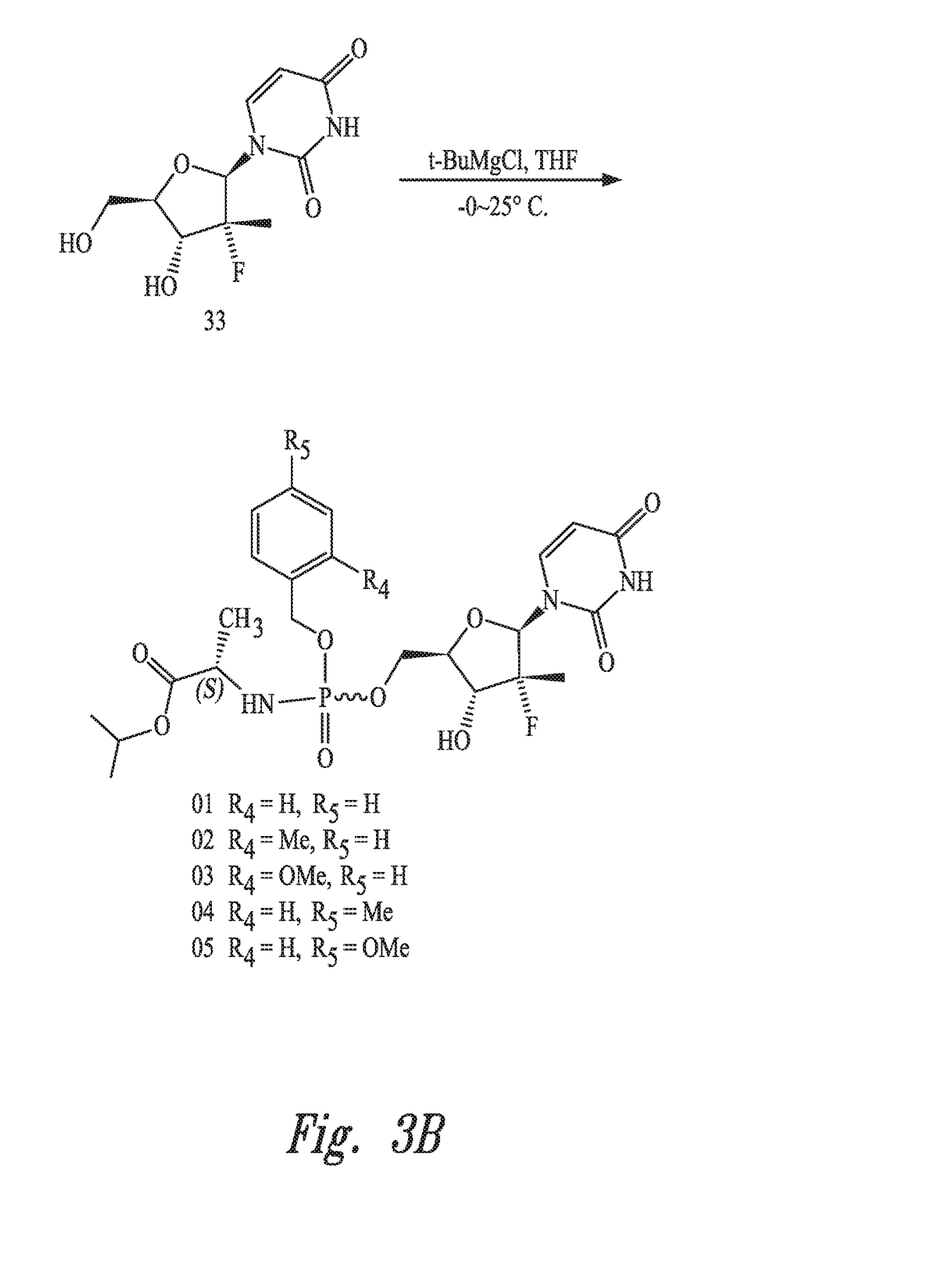
FIG. 3B shows the continuation of synthesis route 1 and generation of a compound selected from the group consisting of compounds 01, 02, 03, 04, and 05, as disclosed in Examples 6 to 10 for preparation method 1.

Synthesis route 1 is disclosed below and shown in FIGS. 3A and 3B.

Figure 3C:
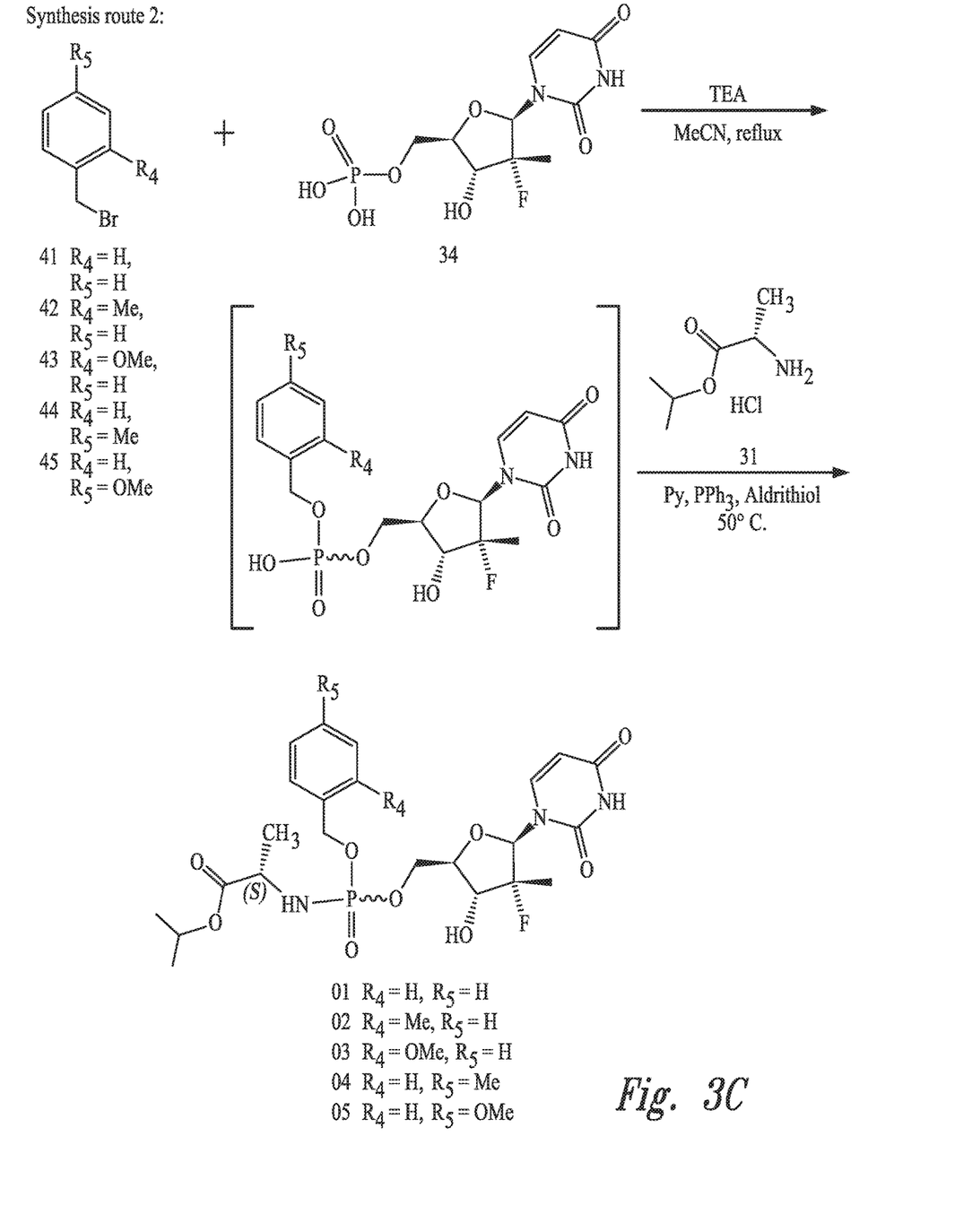
FIG. 3C shows synthesis route 2 and generation of a compound selected from the group consisting of compounds 01, 02, 03, 04, and 05, as disclosed in Examples 6 to 10 for preparation method 2.

Synthesis route 2 is disclosed below and shown in FIG. 3C.

Example 1: Preparation of Compound 21

$POCl_3$ (14.2 g, 92.5 mmol, 1.00 eq) and anhydrous dichloromethane (300 mL) were added to a three-necked bottle, mixed uniformly and then cooled to −40 DEG C. While stirring at this temperature, a mixed solution of compound 11 (see raw material 11 in synthesis route 1, 10.0 g, 92.5 mmol, 1.00 eq) and anhydrous triethylamine (9.36 g, 92.5 mmol, 1.00 eq) in anhydrous dichloromethane (100 mL) was added dropwise over 30 minutes. Then, the temperature was maintained at −78 DEG C. with stirring for 2 hours. At this temperature, compound 31 (14.7 g, 87.8 mmol, 0.95 eq) and anhydrous dichloromethane (50 mL)

were added to the reaction mixture, and then a anhydrous dichloromethane (50 mL) solution of triethylamine (18.7 g, 185 mmol, 2.00 eq) was added dropwise over 30 minutes. After temperature naturally raised to the room temperature, cooling was carried out to 0 DEG C. after stirring for 2 hours. A mixed anhydrous dichloromethane (50 mL) solution of compound 32 (10.2 g, 55.5 mmol, 0.60 eq) and triethylamine (11.2 g, 111 mmol, 1.20 eq) was added dropwise to the reaction mixture over 20 minutes, and then stirred under the room temperature condition overnight (16 hours). Next, the solvent was removed through spin drying under reduced pressure. The residue was treated with water (200 mL) and ethyl acetate (100 mL) for liquid separation, wherein the aqueous phase was further extracted with ethyl acetate (50 mL.times.2) and then mixed with the organic phase, and the organic phase was washed with saline water (50 mL), then dried with anhydrous sodium sulfate, and filtered. After the solvent was removed through spin drying under reduced pressure, column chromatography (silica gel, 200-300 meshes, a volume ratio of ethyl acetate to petroleum ether being 1/10 to 1/1) was performed to obtain white solid 21. The yield was 89.8%.

$^1$H NMR (400 MHz, CDCl$_3$) δ 7.37~7.38 (m, 5H), 5.19~5.23 (m, 2H), 4.99~5.09 (m, 1H), 3.97~4.08 (m, 1H), 3.75-3.84 (m, 1H), 1.41 (dd, J=7.2 Hz, J=12.8 Hz, 3H), 1.22-1.27 (m, 6H); $^{19}$F NMR (400 MHz, CDCl$_3$) δ -153.57~-153.71 (m, 2F), -159.76~-160.01 (m, 1F), -162.15~-162.34 (m, 2F); $^{31}$P NMR (400 MHz, CDCl$_3$) δ 3.91 (s, 1P).

Example 2: Preparation of Compound 22

The preparation method was the same as that of example 1, wherein the compound 11 was replaced by compound 12 (see raw material 12 in synthesis route 1). The yield was 84.9%.

$^1$H NMR (400 MHz, CDCl$_3$) δ 7.36-7.18 (m, 4H), 5.25-5.22 (m, 2H), 5.08-4.97 (m, 1H), 4.07-3.95 (m, 1H), 3.82-3.72 (m, 1H), 2.38, 2.37 (s, s, 3H), 1.43-1.36 (dd, J=20, 8.0 Hz, 3H), 1.27-1.20 (m, 6H); $^{19}$F NMR (400 MHz, CDCl$_3$) δ -153.61~-153.75 (m, 2F), -159.76~-160.01 (m, 1F), -162.14~-162.33 (m, 2F); $^{31}$P NMR (400 MHz, CDCl$_3$) δ 4.02, 3.97 (s, s, 1P).

Example 3: Preparation of Compound 23

The preparation method was the same as that of example 1, wherein the compound 11 was replaced by compound 13 (see raw material 13 in synthesis route 1). The yield was 79.7%.

$^1$H NMR (400 MHz, CDCl$_3$) δ 7.36-7.27 (m, 2H), 6.98-6.94 (m, 1H), 6.90-6.88 (m, 1H), 5.33-5.21 (m, 2H), 5.09-4.99 (m, 1H), 4.10-4.01 (m, 1H), 3.91-3.83 (m, 4H), 1.43 (dd, J=9.2, 7.2 Hz, 3H), 1.28-1.23 (m, 6H); $^{19}$F NMR (400 MHz, CDCl$_3$) δ -153.48~-153.64 (m, 2F), -160.11~-160.35 (m, 1F), -162.40~-162.59 (m, 2F); $^{31}$P NMR (400 MHz, CDCl$_3$) δ 3.96, 3.88 (s, s, 1P).

Example 4: Preparation of Compound 24

The preparation method was the same as that of example 1, wherein the compound 11 was replaced by compound 14 (see raw material 14 in synthesis route 1). The yield was 70.2%.

$^1$H NMR (400 MHz, CDCl$_3$) δ 7.27-7.16 (dd, J=36, 8.0 Hz, 4H), 5.16-5.14 (d, J=8.0 Hz, 2H), 5.05-4.98 (m, 1H), 4.05-3.96 (m, 1H), 3.76-3.71 (m, 1H), 2.36 (3, 3H), 1.43, 1.41 (s, s, 3H), 1.23, 1.22 (s, s, 6H); $^{19}$F NMR (400 MHz, CDCl$_3$) δ -153.63~-153.69 (m, 2F), -160.07~-160.09 (m, 1F), -162.34~-162.44 (m, 2F); $^{31}$P NMR (400 MHz, CDCl$_3$) δ 3.91 (s, 1P).

Example 5: Preparation of Compound 25

The preparation method was the same as that of example 1, wherein the compound 11 was replaced by compound 15 (see raw material 15 in synthesis route 1). The yield was 15.4%.

$^1$H NMR (400 MHz, CDCl$_3$) δ 7.38-7.29 (m, 2H), 6.89-6.85 (m, 1H), 6.80-6.78 (m, 1H), 5.36-5.24 (m, 2H), 5.15-5.04 (m, 1H), 4.12-4.04 (m, 1H), 3.89-3.85 (m, 4H), 1.45 (dd, J=9.2, 7.2 Hz, 3H), 1.27-1.21 (m, 6H); $^{19}$F NMR (400 MHz, CDCl$_3$) δ -153.30~-153.46 (m, 2F), -160.08~-160.32 (m, 1F), -162.59~-162.70 (m, 2F); $^{31}$P NMR (400 MHz, CDCl$_3$) δ 3.95 (s, 1P).

Example 6: Preparation of Compound 01

Method 1:
Under the condition of 0 DEG C., 1 M tert-butyl magnesium chloride (7.5 mmol) was slowly added dropwise to a DMF (20 mL) suspension of compound 33 (5 mmol), reacted for 1 hour at 0 DEG C. after being completely added. Then, a THF solution (20 ml) of the compound 21 (5.75 mmol, prepared in example 1) was slowly added dropwise, reacted for 1 hour at 0 DEG C. after being completely added, and then stirred overnight with the temperature naturally rising to the room temperature. 20 ml ice water was added to the reaction solution and stirred for 0.5 hour for quenching reaction. Then, the reaction solution was extracted with ethyl acetate (3×20 ml), and the organic phase was washed with saline water (20 mL) and then dried with anhydrous sodium sulfate. After filtering and the removal of the solvent through spin drying under reduced pressure, column chromatography (silica gel, 200-300 meshes, methanol/dichloromethane=1l/20) was perfomed to obtain white solid 01. The yield was 58.4%.

Method 2:
DIPEA (10 mmol) and compound 41 (see raw material 41 in synthesis route 2, 5 mmol) were sequentially added to an acetonitrile (20 mL) suspension of compound 34 (5 mmol). The mixture was stirred for 16 hours under heating reflux, and then spin-dried under reduced pressure. Pyridine (20 mL) was added to dissolve the residue, and then triethylamine (5 mL) and compound 31 (see raw material 31 in synthesis route 1, 10 mmol) were sequentially added, heated to 50 DEG C. and stirred for 30 minutes. Then, triphenylphosphine (15 mmol) and 2,2'-dithiopyridine (15 mmol) were added at this temperature, stirred for 3 hours at the temperature of 50 DEG C., and then spin-dried under reduced pressure. Column chromatography (eluting with methanol/dichloromethane) of the residue on silica gel was carried out to obtain white solid product. The yield was 32.6%.

$^1$H NMR (400 MHz, CDCl$_3$) δ 9.47 (br s, 1H), 7.48, 7.46 (s, s, 1H), 7.45-7.34 (m, 5H), 6.19, 6.15 (s, s, 1H), 5.74-5.71 (dd, J=4.0 Hz, 1H), 5.11-4.96 (m, 3H), 4.40-4.29 (m, 3H), 4.09-4.07 (m, 3H), 3.81-3.75 (m, 1H), 1.30-1.29 (s, s, 6H), 1.25-1.21 (m, 6H); $^{19}$F NMR (400 MHz, CDCl$_3$) δ -162.02, -162.35 (s, s, 1F); $^{31}$P NMR (400 MHz, CDCl$_3$) δ 8.72, 8.67 (s, s, 1P).

Example 7: Preparation of Compound 02

Preparation method 1 was the same as method 1 of example 6, wherein the compound 21 was replaced by the compound 22. The yield was 54.2%.

The preparation method 2 was the same as method 2 of example 6, wherein the compound 41 was replaced by compound 42 (see raw material 42 in synthesis route 2). The yield was 30.6%.

$^1$H NMR (400 MHz, CDCl$_3$) δ 9.16 (br s, 1H), 7.47, 7.45 (s, s, 1H), 7.35-7.20 (m, 4H), 6.19, 6.15 (s, s, 1H), 5.73, 5.71 (dd, J=8.0 Hz, 1H), 5.17-4.97 (m, 3H), 4.40-4.23 (m, 3H), 4.09-4.03 (m, 1H), 3.95-3.73 (m, 3H), 2.38 (s, 3H), 1.42-1.28 (m, 6H), 1.23-1.21 (m, 6H); $^{19}$F NMR (400 MHz, CDCl$_3$) δ −163.94 (s, 1F); $^{31}$P NMR (400 MHz, CDCl$_3$) δ 8.79 (s, 1P).

Example 8: Preparation of Compound 03

Preparation method 1 was the same as method 1 of example 6, wherein the compound 21 was replaced by the compound 23. The yield was 48.3%.

The preparation method 2 was the same as method 2 of example 6, wherein the compound 41 was replaced by compound 43 (see raw material 43 in synthesis route 2). The yield was 28.9%.

$^1$H NMR (400 MHz, CDCl$_3$) δ 8.90 (br s, 1H), 7.52-7.49 (m, 1H), 7.37-7.32 (m, 2H), 6.99-6.89 (m, 2H), 6.21, 6.16 (s, s, 1H), 5.75-5.47 (d, d, J=8.0 Hz, J=8.0 Hz, 1H), 5.16-5.08 (m, 2H), 5.05-4.96 (m, 1H), 4.42-4.30 (m, 2H), 4.09-4.07 (m, 1H), 3.95-3.72 (m, 6H), 1.88 (br s, 2H), 1.42-1.34 (m, 6H), 1.25-1.22 (m, 6H); $^{19}$F NMR (400 MHz, CDCl$_3$) δ −162.30, −162.90 (s, s, 1F); $^{31}$P NMR (400 MHz, CDCl$_3$) δ 8.77, 8.71 (s, s, 1P).

Example 9: Preparation of Compound 04

Preparation method 1 was the same as method 1 of example 6, wherein the compound 21 was replaced by the compound 24. The yield was 52.9%.

The preparation method 2 was the same as method 2 of example 6, wherein the compound 41 was replaced by compound 44 (see raw material 44 in synthesis route 2). The yield was 25.3%.

$^1$H NMR (400 MHz, CDCl$_3$) δ 9.06 (br s, 1H), 7.47-7.40 (m, 1H), 7.28-7.16 (m, 4H), 6.99-6.89 (m, 2H), 6.18 (d, J=20 Hz, 1H), 5.71, 5.45 (d, d, J=8.0 Hz, J=8.0 Hz, 1H), 5.09-4.94 (m, 3H), 4.40-4.28 (m, 2H), 4.08-4.06 (m, 1H), 3.95-3.72 (m, 3H), 2.36, 2.34 (s, s, 3H), 1.43-1.22 (m, 12H); $^{19}$F NMR (400 MHz, CDCl$_3$) δ −162.03, −162.45 (s, s, 1F); $^{31}$P NMR (400 MHz, CDCl$_3$) δ 8.73, 8.66 (s, s, 1P).

Example 10: Preparation of Compound 05

Preparation method 1 was the same as method 1 of example 6, wherein the compound 21 was replaced by the compound 25. The yield was 57.3%.

The preparation method 2 was the same as method 2 of example 6, wherein the compound 41 was replaced by compound 45 (see raw material 45 in synthesis route 2). The yield was 22.5%.

$^1$H NMR (400 MHz, CDCl$_3$) δ 8.87 (br s, 1H), 7.55-7.52 (m, 1H), 7.35-7.30 (m, 2H), 6.97-6.86 (m, 2H), 6.19 (d, J=8.0 Hz, 1H), 5.77~5.49 (m, 1H), 5.25-5.18 (m, 2H), 5.12-4.99 (m, 1H), 4.57-4.45 (m, 2H), 4.21-4.17 (m, 1H), 3.98-3.76 (m, 6H), 2.05 (br s, 2H), 1.44-1.32 (m, 6H), 1.24-1.20 (m, 6H); $^{19}$F NMR (400 MHz, CDCl$_3$) δ −162.30, −162.90 (s, s, 1F); $^{31}$P NMR (400 MHz, CDCl$_3$) δ 8.77, 8.71 (s, s, 1P).

Example 11: Separation and Preparation of Single Chiral Compounds

HPLC reversed phase column separation: the compound 01 in example 6 was subjected to HPLC preparative separation (preparative column: Diamonsil C18, 5 μm, 150×21.1 mm; mobile phase: 20% aqueous solution of acetonitrile (V/V)) and isocratic elution, and then compounds 01b and 01a were obtained sequentially according to the peak appearance sequence.

HPLC chiral column separation: the compound 01 in example 6 was subjected to chiral column preparative separation (preparative column: CHIRALPAK AD-H, 0.46 cm I.D.×25 cm L; mobile phase: n-hexane/isopropanol=65/35 (V/V) and isocratic elution, and then compounds 01b and 01a were obtained sequentially according to the peak appearance sequence.

compound 01a: $^1$H NMR (400 MHz, CDCl$_3$) δ 9.07 (br s, 1H), 7.42-7.33 (m, 6H), 6.19, 6.15 (d, J=16 Hz, 1H), 5.46, 5.44 (d, J=8.0 Hz, 1H), 5.12-4.98 (m, 3H), 4.40, 4.39 (d, J=4.0 Hz, 2H), 4.09, 4.07 (d, J=8.0 Hz, 1H), 3.92-3.73 (m, 4H), 1.39-1.33 (m, 6H), 1.24, 1.22 (d, J=8.0 Hz, 6H); $^{19}$F NMR (400 MHz, CDCl$_3$) δ −162.47 (s, 1F); $^{31}$P NMR (400 MHz, CDCl$_3$) δ 8.70 (s, 1P).

compound 01b: $^1$H NMR (400 MHz, CDCl$_3$) δ 8.97 (br s, 1H), 7.48, 7.46 (s, s, 1H), 7.42-7.36 (m, 5H), 6.19, 6.15 (s, s, 1H), 5.74, 5.72 (d, J=8.0 Hz, 1H), 5.14-4.97 (m, 3H), 4.41-4.29 (m, 2H), 4.14-3.73 (m, 5H), 1.43-1.22 (m, 12H); $^{19}$F NMR (400 MHz, CDCl$_3$) δ −162.02 (s, 1F); $^{31}$P NMR (400 MHz, CDCl$_3$) δ 8.77 (s, 1P).

For a prodrug compound, the most important is the stability of the prodrug in a non-target organ system and the metabolic activity thereof in the target organ part. The higher the stability in a system (such as gastrointestinal tract, blood and the like) is, the higher the amount of the active compound from metabolism in a target organ (such as the liver in the invention and the like) is, with lower toxicity and higher efficacy of the compound. In assays, the prodrugs such as the compounds of the present invention and the control compounds are all metabolized into the active metabolite uridine triphosphoric acid so as to play the anti-HCV effect.

At present, structurally similar prodrug compounds include a compound (hereinafter referred to as patent compound 06 in 2008) disclosed in example 25 of CN101918424A (Application No. 200880103023.8), single chiral isomers thereof (hereinafter referred to as patent compound 06a, patent compound 06b in 2010) disclosed in CN102459299A (Application No. 201080032541.2), and a compound (see the compound before the second and third compounds in the right column of page 39 in claim 15 of the disclosure are separated, hereinafter referred to as unresolved enantiomer 02 of patent compounds in 2013) disclosed in U.S. Pat. No. 9,156,874. Such compounds and the compounds of the present invention have the same parent drug structure 2-fluoro-2-methyldeoxyuridine and the same active metabolic product 2-fluoro-2-methyldeoxyuridine triphosphoric acid, but different liver targeting fragments.

In theory, the compounds of the present invention has the advantage of comparable or higher activity, or lower systemic toxicity due to more stable structure in the blood system. Furthermore, compared with the patent compound 06 in 2008, the benzoic acid compounds generated by the metabolism of the compounds of the present invention are relatively safe, overcome the defect that the patent compound 06 in 2008 releases toxic phenol, and has the advantage of being relatively low in toxicity while being excellent in activity. Further, compared with the unresolved enantiomer 02 of patent compounds in 2013, since the non-o-methyl substituted benzyl group in the liver targeting fragments of the compounds of the present invention are more stable than o-methyl benzyl and the shedding activity of the benzyl is relatively low in blood esterase metabolism, the active parent drug in blood is relatively reduced while active metabolite in liver is relatively increased, thereby reflecting better activity. After the shedding of the benzyl, the compounds of the present invention may have lower toxicity and better system stability, and such guesses have been supported and verified by data in practical research. Details are shown in the following assays.

Assay 1: Contrast Experiments of Anti-HBV Activity and Cytotoxicity on Cellular Level A hepatitis C virus (HCV) genotype (GT) 1b stable transfection replicon cell line system was used to determine the inhibitory activity of the compounds to the HCV GT1b replicons. In this experiment, the compound 06a (GS-7977) was used as a control compound to monitor the experimental quality.

1. Compound Structure

The tested compounds were compounds 01, 03, 04, 05 enumerated in the examples of the present invention.

Compound 01 was resolved to obtain single chiral isomers 01a, 01 b. The control compound was the patent compound 06 in 2008, the patent compound 06a in 2010, and the unresolved enantiomer 02 in 2013.

06

06a
(Sofosbuvir, GS-7977)

02

2. Compound dilution: 20 mM mother liquor was prepared by using 100% DMSO, and the compound DMSO mother liquor was diluted and added to a 96-well experiment plate. The final concentration of the DMSO was 0.5%. In in-vitro anti-HCV activity experiments and cytotoxicity experiments, all compounds had the initial concentration of 20 microns, and were diluted by 5 times of dilution. The final concentration of the DMSO of 6 concentrations were 0.5%.

3. Cell treatment: HCV-1b replicon sub-cells were added to the above 96-well cell plate (8,000 cells/well), and then placed into an incubator of 37 DEG C. and 5% $CO_2$ for culturing for 3 days.

4. Cell activity detection: a cell growth fluorescent titration detection reagent was added to each well; after the cells were cultured for 1 hour in the incubator of 37 DEG C. and 5% $CO_2$, a spectrophotometer detection system Envision was used to detect a Fluorescence signal value. The original data, i.e, relative fluorescence units (RFUs), was used for the calculation of the cell toxicity of the compounds.

5. Anti-HCV replicon activity detection: a luciferase light-emitting substrate bright-GLO was added to each well, and a chemiluminescence detection system Envision was used for detecting a Luminescence signal value in 5 minutes. The original data, i.e., relative light units (RLUs), was used for the calculation of the inhibitory activity of the compounds.

6. Data processing: the RFUs obtained in step 1.3 were processed into a cell activity percentage by using the following formula:

$$\text{Viability\%} = \frac{CPD}{ZPE} \times 100.$$

The RLUs obtained in step 1.4 were processed into a inhibition percentage by using the following formula:

$$\text{Inhibition \%} = \frac{ZPE - CPD}{ZPE - HPE} \times 100\%$$

*CPD: signal values of compound wells
HPE (high percent effect): 100% effective action control well signal value, with only DMEM culture solution in the wells;
The ZPE (zero percent effect): noneffective control well signal value, with 0.5% DMSO to replace the compound.

The cell activity percentage and the inhibition percentage were respectively imported into GraphPad Prism software for data processing to obtain curves corresponding to the compounds and their values of cytotoxicity ($CC_{50}$) and inhibitory activity ($ECD_{50}$) to the HCV replicons.

7. Experiment Results and Conclusions:

TABLE 1

Anti-HCV replicon activity $EC_{50}$ values and cytotoxicity $CC_{50}$ values to HCV GT1b replicons of compounds

| | HCV GT1b replicons | |
| Compounds | $EC_{50}$ (μM) | $CC_{50}$ (μM) |
| --- | --- | --- |
| 01 | 6.115 | >20 |
| 03 | >20 | >20 |
| 04 | 15.23 | >20 |
| 05 | >20 | >20 |
| Patent compound 06 in 2008 | 9.820 | >20 |
| Unresolved enantiomer 02 of patent compounds in 2013 | 17.69 | >20 |
| 01a | 0.3009 | >20 |
| 01b | 9.146 | >20 |
| Patent compound 06a in 2010 | 0.7192 | >3 |

There were 6 tested compounds and 3 control compounds in this experiment, and experimental results are summarized as follows:

The test compound 01 and the control compound 06 (patent compound 06 in 2008) exhibited good activity of inhibiting HCV GT1b, with the $EC_{50}$ values below 10 μM. The activity of the compound 01 was superior to that of the control compound 06. The tested compound 04 and the control compound 02 (the unresolved enantiomer 02 of patent compounds in 2013) was relatively weak in the activity of inhibiting HCV GT1b replication, with the $EC_{50}$ value between 10 μM to 20 μM. The $EC_{50}$ values of the HCV GT1b replication inhibiting activity of the other two tested compounds 03, 05 were higher than the maximum test concentration 20 μM.

The compound 01, 03, 04, 05 were similar in structure to the control compound 02, 06 and thus had similar effects, wherein the activity of the compound 01 for inhibiting HCV GT1b replication was slightly superior to that of the patent compound 06 in 2008 and the patent compound 02 in 2013, and the activity of the compound 04 was slightly better than that of the unresolved enantiomer 02 of patent compounds in 2013. Single chiral enantiomer compound 01a, 01b and 06a of compounds 01, 06 were selected for activity comparison, indicating that the activity of the single chiral isomer 01a for inhibiting the replication of HCV GT1b was slightly superior to that of the patent compound 06a in 2010.

Assay 2: Stability Research Results

The stability testing method was carried out according to the prior art, and the data displayed in the table was the residual percentages of the tested compounds after incubation for different time periods under the test conditions.

1. Simulated Gastric Liquid Stability (Test Concentration: 10 μM), See Table 2:

TABLE 2

Simulated gastric liquid stability (test concentration: 10 μM)

| Compounds | % 0 h | % 1 h | % 2 h | % 6 h | % 24 h |
| --- | --- | --- | --- | --- | --- |
| 01 | 100 | 96.81 | 105.99 | 100.76 | 71.32 |
| Unresolved enantiomer 02 of patent compounds in 2013 | 100 | 82.70 | 82.45 | 74.80 | 41.56 |
| Patent compound 06 in 2008 | 100 | 95.19 | 98.47 | 84.08 | 49.36 |
| Omeprazole 20 μM | 100 | 5.24 | 2.76 | 0.20 | 0.00 |

2. Simulated Intestinal Fluid Stability (Test Concentration: 10 μM), See Table 3:

TABLE 3

Simulated gastric liquid stability (test concentration: 10 μM)

| Compounds | % 0 h | % 1 h | % 2 h | % 6 h | % 24 h |
| --- | --- | --- | --- | --- | --- |
| 01 | 100 | 1.69 | 0.08 | 0.00 | 0.00 |
| Unresolved enantiomer 02 of patent compounds in 2013 | 100 | 0.63 | 0.08 | 0.00 | 0.00 |
| Patent compound 06 in 2008 | 100 | 0.00 | 0.00 | 0.00 | 0.00 |
| Chlorambucil | 100 | 43.83 | 3.91 | 0.00 | 0.00 |

3. Human Plasma Stability (Test Concentration: 2 μM), See Table 4.

TABLE 4 human plasma stability (test concentration: 2 μM)

| Compounds | % 0 min | % 10 min | % 30 min | % 60 min | % 120 min |
| --- | --- | --- | --- | --- | --- |
| 01 | 100 | 98.9 | 81.7 | 80.9 | 74.9 |
| Unresolved enantiomer 02 of patent compounds in 2013 | 100 | 73.3 | 69.5 | 62.8 | 58.8 |
| Patent compound 06 in 2008 | 100 | 78.8 | 70.9 | 72.0 | 65.3 |
| Propantheline | 100 | 53.3 | 14.3 | 2.2 | 0.0 |

4. Human Liver S9 Stability Parameters (Test Concentration: 1 μM), See Table 5.

TABLE 5

Human liver S9 stability parameters (test concentration: 1 μM)

| Compounds | $T_{1/2\ min}$ | $CL_{int(s9)}$ uL/min/mg | $CL_{int(s9)}$ uL/min/kg | Remaining % (T = 1 h) | Remaining % (NCF = 1 h) |
| --- | --- | --- | --- | --- | --- |
| 01 | 96.6 | 7.2 | 25.2 | 56.2 | 67.4 |
| Unresolved enantiomer 02 of patent compounds in 2013 | 9.5 | 72.6 | 255.6 | 1.1 | 64.7 |
| Patent compound 06 in 2008 | 115.4 | 6.0 | 21.1 | 58.6 | 64.0 |
| 7-Ethoxycumarin | 3.6 | 194.2 | 683.5 | 0.0 | 103.3 |
| 7-Hydroxycoumarin | 96.6 | 7.2 | 25.2 | 56.2 | 67.4 |

The effectiveness of the series of experiments could be verified through experimental data of the above 7-Ethoxycumarin, 7-Hydroxycoumarin, Propantheline, Chlorambucil, and Omeprazole relative to the controls.

The preliminary research experiment data on the stability showed that the compound 01 was higher than the unresolved enantiomer 02 of patent compounds in 2013 and the patent compound 06 in 2008 in the stability in gastric liquid, simulated intestinal liquid and human blood. In the human liver s9, the compound 01 was equivalent to the patent compound 06 in 2008 in stability and in the rate of metabolization into the active mother drug, indicating that the compounds of the same concentration in the liver cells had equivalent activity.

By comprehensive comparison, the compound 01 had higher gastrointestinal tract and blood system metabolism stability than the compounds 02, 06, so that the drug concentration of the non-focus part was lower, and the drug concentration in the focus part was higher, indicating that the compound 01 has better liver targeting performance and lower system toxicity in vivo than the unresolved enantiomer 02 of patent compounds in 2013 and the patent compound 06 in 2008.

Assay 3: In-Vitro Heart Toxicity Research

1, Preparation of Experimental Cells and Compounds

The experiment adopted CHO cells which can stably express the herg potassium ion channel from AVivaBiosciences company, wherein the cells were incubated in a constant-humidity environment at the temperature of 37 DEG C. with 5% $CO_2$.

The compounds and the positive control compounds (amitriptyline, sigma-aldrich, BCBJ8594V) were dissolved in 100% dimethyl sulfoxide (DMSO) and then isocratically diluted, with the final concentration of the DMSO DMSO in the extracellular fluid not higher than 0.30%, and stored at −20 DEG C. for later use.

2, Manual Diaphragm Clamp Records

The compounds were tested on a Multiclamp patch-clamp amplifier at room temperature; the output signals were digitized by using a DLigital 1440 A/D-D/A board; the PCLAMP 10 software was used for recording and controlling. The minimum sealing resistance was set to 500 MOhms and the minimum specific hERG current was set to 0.4 nA for quality control.

3, Data Analysis

Clampfit (V10.2, Molecular Devices), Excel 2003 and GraphPad Prism 5.0 were used for data analysis. Current calculation formula:

$$I/I_{control} = Bottom + (Top - Bottom)/(1 + 10^{((Log\ IC50 - Log\ C)*Hillslope)})$$

4. Experimental Results and Conclusions: See Table 6

TABLE 6

Resullts of in vitro cardiotoxicity experiment

| Compounds | $IC_{50}$ (μM) | HillSlope | Number of cells |
|---|---|---|---|
| Amitriptyline | 3.19 | 1.18 | 4 |
| 01a | >30.00 | — | 2 |
| 01b | >30.00 | — | 2 |
| Patent compound 06a in 2010 | >10.00 | — | 2 |

Conclusions: in the hERG experiment, the compounds 01a and 01b both had the $IC_{50}$ above 10 μM and the compound 06a had the $IC_{50}$ above 10 μM too, indicating that at the same dosage, the compounds 01a and 01b are slightly better in the safety of causing heart toxicity than the patent compound 06a in 2010.

Assay 4: In-Vivo Metabolism and Tissue Distribution Experiment of Rats

1, Experimental Animal, Drug Preparation Method and Drug Delivery Scheme

18 SD rats (male, 6-9 weeks old, purchased from Vital River Animal center) were divided into 6 groups randomly, 3 rats in each group, fasted for 12 hours first before administration, freely fed with water during the fasting period. After the administration is carried out for 4 hours, the fasting was ended. 50 mg compound was precisely weighed on a balance, and 95% (0.5% of cd))/5% solutol aqueous solution was added and uniformly mixed, and subjected to ultrasonic treatment for later use. The drug delivery dose was 50 mg/kg; the drug delivery concentration was 10 mg/kg; and the drug delivery volume was 5 mg·kg.

2. Sample Collection Scheme and Processing Method

The sample collection scheme: taking blood and liver tissues after carrying out intragastric administration on rats for 1 h, 2 h, 3 h, 6 h, 12 h and 24 h.

The plasma sample processing method: transferring the whole blood of the rats to a centrifugal EP tube which was added with 3 muL/0.5 m of $k_2$ EDTA as an anticoagulant, immediately adding 200 μL whole blood into an EP tube containing 800 μL pre-cooled 75% MeOH/25% CAN and the internal standard (V75% MeOH/25% ACN:VBlood=4:1), so that the protein is precipitated and the stability of the tested object in whole blood was ensured. After the sample was subjected to vortex oscillation for 2 minutes, the sample was centrifuged for 15 minutes under the conditions of about 4 DEG C. and 12,000 rpm, thereby separating 75% MeOH/25% acetonicle extract and the cell/protein fragments. The sample was stored at −70 DEG c. The supernate was taken for 30 μL and added with 30 μL water for vortex mixing. The mixture was centrifuged at the temperature of 4 DEG C., and a supernate of 5 μL was taken for LC/MS/MS analysis.

The liver tissue sample treatment method: taking a rat tissue sample in a plastic EP tube, and adding 5 times (w:v) 1.75 mL MeOH and 5 μL 50% KOH aqueous solution together with 0.75 mL 268 mM EDTA solution to prepare a solution, uniformly mixing and taking 60 μL sample, adding a 240 μL internal standard solution for mixing, carrying out vortex oscillation for 2 minutes, and centrifuging for 10 minutes (13000 rpm and 4 DEG C.), taking 30 μL of supernate, adding 30 μL of water, carrying out vortex mixing, centrifuging at 4 DEG C., and then taking 5 μL supernate for LLC/MS/MS analysis.

3. The Sample Analysis Method

LC-MS/MS-O (API 4000) liquid mass spectrometer and chromatographic column are adopted: ACQUITY UPLC BEH C18 130 Å 1.7 μm 2.1×50 mm the composition com: and tomitamide was adopted as an internal standard compound, gradient elution analysis is carried out after the sample is fed into the sample, and the internal standard is recorded respectively, the retention time and the peak area of the to-be-tested compound and the metabolite TSL 1100, the software phoenix winnonlin 6.2. The method is analyzed by an srms quantitative detection method.

4. Analysis Results of the Sample and the Conclusion are as Follows: See Table 7.

TABLE 7

PK parameters of metabolites in liver tissue after intragastric administration of rats
PK Parameters of TSL1100 in Liver (Rat PO 50 mg/kg)

| PK Parameters | Compounds | |
|---|---|---|
|  | 01a | 01b |
| Rsq_adj | 0.933 | 0.995 |
| No. points used for $T_{1/2}$ | 3.00 | 3.00 |
| $C_{max}$ (ng/mL) | 1340 | 531 |
| $T_{max}$ (h) | 4.00 | 2.00 |
| $T_{1/2}$ (h) | 5.25 | 2.63 |
| $T_{last}$ (h) | 24.0 | 12.0 |
| $AUC_{0-last}$ (ng · h/mL or ng · h/g) | 10501 | 3217 |
| $AUC_{0-inf}$ (ng · h/mL or ng · h/g) | 11024 | 3445 |
| $MRT_{0-last}$ (h) | 6.77 | 4.54 |
| $MRT_{0-inf}$ (h) | 7.94 | 5.28 |
| $AUC_{Extra}$ (%) | 4.74 | 6.61 |
| $AUMC_{Extra}$ (%) | 18.9 | 19.8 |
| AUC Ratio | ND | ND |

The results of table 7 showed that: no triphosphate active metabolites were completely detected in whole blood and an active metabolite was detected in the liver. The PK parameters of the active metabolite were as shown in the following table. The results showed that the compound could be effectively enriched and converted into an active metabolite in the liver. The liver targeting property was verified, and the anti-HCV activity was indicated.

The representative compounds selected in the assays showed that the novel uridine phosphoryl amine prodrug compound could be used for preparing medicaments for treating hepatitis c virus infectious diseases.

Although the invention has been described in detail above in terms of general description, specific implementation manners and assays, it will be apparent to those skilled in the art that the invention can be modified or improved on the basis of the invention. Accordingly, these modifications and improvements made without departing from the spirit of the invention all fall into the protection scope of the invention.

The invention claimed is:

1. A prodrug having a structure of compound 01

01 or a solvate, pharmaceutically acceptable salt, and/or optical isomer thereof.

2. A preparation method for the prodrug of claim 1, comprising the steps of reacting phosphorus oxychloride with benzyl alcohol in the presence of a base, and then with a compound having the structure of formula 31

31 and an active aromatic reagent having the structure of formula (ii), (ii)

wherein Y is O, S or Se; $R_4$ is hydrogen or a suitable silicon-containing or fluorine-containing leaving group; W is halogen or nitro; and n is an integer from 0 to 5; to obtain a phosphate ester intermediate; and reacting the phosphate ester intermediate with a uridine analogue 33

33 in the presence of a base to generate a uridine phosphoramide prodrug having the structure of compound 01 or a solvate, pharmaceutically acceptable salt, and/or optical isomer thereof.

3. A preparation method for the prodrug of claim 1, comprising the steps of reacting uridine monophosphate having the structure of compound 34

34 with benzyl alcohol in the presence of a base to obtain a uridine monophosphate intermediate; and reacting the uridine monophosphate intermediate with a compound having the structure of formula 31

31 in the presence of a condensing agent to generate a uridine phosphoramide prodrug having the structure of compound 01;

or a solvate, pharmaceutically acceptable salt, and/or optical isomer thereof.

4. A pharmaceutical composition, comprising the prodrug of claim 1 and a pharmaceutically acceptable carrier.

5. The prodrug of claim 1, wherein the prodrug is an enantiomer having a single phosphate chiral configuration.

* * * * *